US011547767B2

(12) United States Patent
Ferro Flores et al.

(10) Patent No.: US 11,547,767 B2
(45) Date of Patent: *Jan. 10, 2023

(54) $^{99m}$TC-EDDA/HYNIC-IPSMA AS A RADIOPHARMACEUTICAL FOR DETECTING THE OVEREXPRESSION OF PROSTATE-SPECIFIC MEMBRANE ANTIGEN (71) Applicant: INSTITUTO NACIONAL DE INVESTIGACIONES NUCLEARES, Estado de México (MX)

(72) Inventors: Guillermina Ferro Flores, Estado de México (MX); Blanca Eli Ocampo Garcia, Estado de México (MX); Clara Leticia Santos Cuevas, Estado de México (MX); Myrna Alejandra Luna Gutiérrez, Estado de México (MX); Erika Patricia Azorin Vega, Estado de México (MX); Nallely Patricia Jiménez Mancilla, Estado de México (MX)

(73) Assignee: Instituto Nacional de Investigaciones Nucleares, Ocoyoacac (MX)

( * ) Notice: Subject to any disclaimer, the term of this patent is extended or adjusted under 35 U.S.C. 154(b) by 42 days.

This patent is subject to a terminal disclaimer.

(21) Appl. No.: 17/135,424

(22) Filed: Dec. 28, 2020

(65) Prior Publication Data
US 2021/0187132 A1 Jun. 24, 2021

Related U.S. Application Data (63) Continuation of application No. 16/310,744, filed as application No. PCT/MX2017/000068 on Jun. 21, 2017, now Pat. No. 10,918,745.

(30) Foreign Application Priority Data
Jun. 24, 2016 (MX) .................... MX/a/2016/008466

(51) Int. Cl.
*A61K 51/04* (2006.01)
*A61P 35/04* (2006.01)
(52) U.S. Cl.
CPC .......... *A61K 51/0478* (2013.01); *A61P 35/04* (2018.01)
(58) Field of Classification Search
None
See application file for complete search history.

(56) References Cited

U.S. PATENT DOCUMENTS

| 9,044,468 B2 | 6/2015 | Pomper et al. |
| 9,694,091 B2 | 7/2017 | Pomper et al. |
| 2011/0064657 A1 | 3/2011 | Pomper et al. |
| 2015/0246144 A1 | 9/2015 | Pomper et al. |

FOREIGN PATENT DOCUMENTS

| CN | 102949735 A | 3/2013 |
| CN | 104244991 A | 12/2014 |
| MX | 2010/003830 A | 10/2011 |
| WO | 2009002529 A2 | 12/2008 |
| WO | 2016062370 A1 | 4/2016 |

OTHER PUBLICATIONS

Chinese Office Action and Search Report dated Nov. 4, 2020 from Chinese Patent Appln. No. 201780049494.4.
Ferro-Flores et al. Clinical translation of a PSMA inhibitor for 99mTc-based SPECT. May 2017 Nucl. Med. Biol. 48: 36-44.
Supplementary European Search Report dated Feb. 12, 2020 in European Patent Appin. No. 17815772.3.
Kakali et al., "Radiolabeled Novel Peptide for Imaging Somatostatin-Receptor Expressing Tumor: Synthesis and Radiobiological Evaluation," Journal of Radioanalytical and Nuclear Chemistry, vol. 301, No. 3, Jun. 8, 2014, pp. 847-861.
Hillier, S.M. et al. 99mTc-labeled small-molecule inhibitors of prostate-specific membrane antigen for molecular imaging of prostate cancer. Journal of Nuclear Medicine, Aug. 2013, vol. 54, N° 8, 1369-1371.
PCT International Search Report and Written Opinion dated Nov. 3, 2017 for PCT International Patent Application No. PCT/MX2017/000068, 8 pages.
First Examination Report dated Feb. 17, 2021 in connection with Indian Application No. 201817049002.
Mozaffari S et al., entitled "Synthesis and Preliminary Evaluation of a New 99mTc Labeled Substance P Analogue as a Potential Tumor Imaging Agent," Iranian Journal of Pharmaceutical Research (2015). 14 (1):97-110.

*Primary Examiner* — Jennifer Lamberski
(74) *Attorney, Agent, or Firm* — Amster, Rotstein & Ebenstein LLP (57) ABSTRACT

The invention relates to a novel radiopharmaceutical that inhibits the prostate-specific membrane antigen (iPSMA), containing hydrazinonicotinamide (HYNIC) as a critical chemical group in increasing in the lipophilicity of the molecule for binding to the hydrophobic sites of the PSMA, combined with the conventional use of HYNIC as a chelating agent for radiometal $^{99m}$Tc, in which the ethylenediaminetetraacetic acid (EDDA) is used to complete the coordination sphere of the radiometal. The novel radiopharmaceutical $^{99m}$Tc-EDDA/HYNIC-iPSMA detects, with high affinity and sensitivity in vivo, the overexpressed PSMA protein in prostate cancer cells using SPECT molecular imaging techniques in nuclear medicine. The aim of the invention is to provide a novel specific radiopharmaceutical (radiopharmaceutical for molecular targets) for SPECT, with high sensitivity for the detection of tumours with overexpression of PSMA.

7 Claims, 6 Drawing Sheets

Normal distribution (healthy volunteer)

$^{99m}$TC-EDDA/HYNIC-IPSMA AS A RADIOPHARMACEUTICAL FOR DETECTING THE OVEREXPRESSION OF PROSTATE-SPECIFIC MEMBRANE ANTIGEN

CROSS-REFERENCE TO RELATED APPLICATIONS

This application is a continuation of U.S. patent application Ser. No. 16/310,744, filed Dec. 17, 2018, now allowed, which is the U.S. national stage entry under 35 U.S.C. § 371 of PCT International Patent Application No. PCT/MX2017/000068, filed Jun. 21, 2017, which claims priority to Mexican Patent Application No. MX/a/2016/008466, filed Jun. 24, 2016, the contents of which are incorporated herein by reference in their entirety.

TECHNICAL FIELD OF THE INVENTION

The present invention relates to a new radiopharmaceutical that is an inhibitor of the prostate-specific membrane antigen (iPSMA) that contains hydrazinonicotinamide (HYNIC) as a chemical group critical in increasing the lipophilicity of the molecule for coupling to the hydrophobic sites of PSMA, combined with the conventional use of HYNIC as a chelating agent for the radiometal $^{99m}$Tc, where ethylenediaminediacetic acid (EDDA) is used for completing the coordination sphere of the radiometal. The new $^{99m}$Tc-EDDA/HYNIC-iPSMA radiopharmaceutical detects, with high affinity in vivo, the protein PSMA overexpressed in prostate cancer cells by SPECT molecular imaging techniques in nuclear medicine.

BACKGROUND

Prostate cancer (PCa) is the second commonest cancer in men worldwide [Jemal A. et al. *Cancer statistics, 2010. CA Cancer J Clin.* 2010, 60: 277-300]. In patients with localized PCa, the five-year survival rate approaches 100%; however, in patients with metastasis, the five-year survival rate is 31% [Wei Q. et al. *Global analysis of differentially expressed genes in androgen-independent prostate cancer. Prostate Cancer Prostatic Dis.* 2007, 10: 167-174]. Nearly all patients with metastasis respond well initially to antiandrogen treatments. However, the main cause of death in patients with PCa is progression to androgen-independent status.

The enzyme glutamate carboxypeptidase II, also known as prostate-specific membrane antigen (PSMA), is expressed in the epithelial cells of the prostate and is highly overexpressed in 95% of advanced prostate cancers. The expression levels of PSMA are directly correlated with androgen-independence, metastasis and progression of PCa [Santoni M. et al. *Targeting prostate-specific membrane antigen for personalized therapies in prostate cancer: morphologic and molecular backgrounds and future promises. J Biol Regul Homeost Agents.* 2014, 28: 555-563]. Therefore PSMA is a suitable molecular target for detection by imaging and radiotherapy of metastatic prostate cancer using specific radiopharmaceuticals.

The PSMA gene is made up of 19 exons that comprise ~60 kb of the genomic DNA. This gene encodes a type II transmembrane protein with a short cytoplasmic fragment (19 amino acids), a hydrophobic transmembrane domain (24 amino acids), and a large extracellular domain (707 amino acids). PSMA contains Zn in the active center of the enzyme, therefore the sequence Glu-NH—CO—NH-Lys(β-naphthyl alanine)=Glu-Urea-Lys(NaI) has been proposed as an effective inhibitor of its activity [Benesová, M. et al. *Preclinical evaluation of a tailor-made DOTA-conjugated PSMA inhibitor with optimized linker moiety for imaging and endoradiotherapy of prostate cancer. J Nucl Med,* 58, 2015: 914-920]. In the specific chemical interaction, the 3 carboxyl groups of the Glu-Urea-Lys fragment interact electrostatically with the peptide side chains in the active center of PSMA, the oxygen of the urea coordinates with the zinc and the aromatic structure in NaI interacts for coupling with the hydrophobic active site of the enzyme. In recent clinical studies, the application of two different derivatives of iPSMA labeled with Lu-177 showed a significant decrease in the levels of prostate-specific antigen (PSA) in 70-80% of patients with PCa, without showing severe side-effects, significantly increasing the survival of the patients [Ahmadzadehfar H. et al. *Early side-effects and first results of radioligand therapy with $^{177}$Lu-DKFZ-617 PSMA of castrate-resistant metastatic prostate cancer: a two-centre study. EJNMMI Res.* 2015, 5:36 doi: 10.1186/s13550-015-0114-2; Kratochwil C. et al. [$^{177}$Lu]*Lutetium-labelled PSMA ligand-induced remission in a patient with metastatic prostate cancer. Eur J Nucl Med Mol Imaging,* 42, 2015: 987-988; Baum, Richard P., et al. *Lutetium-177 PSMA radioligand therapy of metastatic castration-resistant prostate cancer: safety and efficacy. J Nucl Med,* 2016: DOI: doi:10.2967/jnumed.115.168443; Kratochwil, C. et al. *PSMA-targeted radionuclide therapy of metastatic castration-resistant prostate cancer with Lu-177 labeled PSMA-617. J Nucl Med,* 2016: doi:10.2967/jnumed.115.171397; Rahbar, K. et al. *Response and tolerability of a single dose of $^{177}$Lu-PSMA-617 in patients with metastatic castration-resistant prostate cancer: a multicenter retrospective analysis. J Nucl Med,* 2016: doi: 10.2967/jnumed.116.173757]. The protein PSMA is multifunctional, since it can act as an internalization receptor, as an enzyme of absorption of nutrients, or as a peptidase that participates in signal transduction in epithelial cells and in cellular migration [Rajasekaran A. et al. *Is prostate-specific membrane antigen a multifunctional protein? American Journal of Physiology—Cell Physiology,* 2005, 288:C975-C981]. Therefore the PSMA inhibitor radiopharmaceuticals may also be used in another type of neoplasms different from PCa, such as in the case of metastatic breast cancer, osteosarcomas, gliomas and differentiated thyroid cancer, among others [la Fougère, et al. *In vivo visualization of prostate-specific membrane antigen in glioblastoma. Eur J Nucl Med and Mol Imaging,* 2015, 42: 170-171; Verburg F A, et al. *First evidence of PSMA expression in differentiated thyroid cancer using [68Ga] PSMA-HBED-CC PET/CT. Eur J Nucl Med and Mol imaging,* 2015, 42: 1622-1623; Zeng C. et al. *Prostate-specific membrane antigen: a new potential prognostic marker of osteosarcoma. Medical Oncology,* 2012, 29: 2234-2239; Sathekge M. et al. $^{68}$*Ga-PSMA imaging of metastatic breast cancer.* (2015). *Eur J Nucl Med and Mol imaging,* 2015, 42:1482-1483].

However, before any radiotherapy treatment, the capture of the radiopharmaceutical in the tumors or their metastases must be evaluated by nuclear magnetic imaging in order to confirm whether the treatment will or will not be useful for the patient, as well as for determining the activity required to be administered for imparting the radiation dose for tumor ablation, i.e. personalized medicine is practised. Therefore it is necessary to use PSMA-inhibiting diagnostic radiopharmaceuticals with the aim of obtaining molecular images by positron emission tomography (PET) or by single-photon emission tomography (SPECT). Of these two techniques, PET gives higher spatial resolution and higher sensitivity, therefore the majority of the commercial PSMA-inhibiting diagnostic radiopharmaceuticals have been developed on the basis of $^{68}$Ga, which is a radionuclide for PET [Eder M. et al. *Novel preclinical and radiopharmaceutical aspects of [68Ga]Ga-PSMA-HBED-CC: a new PET tracer for imaging of prostate cancer. Pharmaceuticals,* 2014, 7: 779-796: Eder M. et al. *68Ga-complex lipophilicity and the targeting property of a urea-based PSMA inhibitor for PET imaging. Bioconjugate Chem,* 2012, 23: 688-697; Weineisen et al. *68Ga- and 177Lu-labeled PSMA I&T: optimization of a PSMA-targeted theranostic concept and first proof-of-concept human studies." J Nucl Med,* 2015, 56: 1169-1176; Afshar-Oromieh, A. et al. *Comparison of PET/CT and PET/MRI hybrid systems using a 68Ga-labelled PSMA ligand for the diagnosis of recurrent prostate cancer: initial experience. Eur J Nucl Med and Molecular Imaging* 41.5 (2014): 887-897].

However, at national and international level, studies by SPECT represent more than 70% of the total in nuclear medicine owing to its lower cost and greater availability of equipment and radionuclides, since it is not necessary to have a cyclotron within the hospitals or near them. For SPECT images, the radionuclide most used is $^{99m}$Tc, and there is no publication devoted to a complete clinical study with PSMA inhibitors labeled with $^{99m}$Tc, for which it has only been investigated up to preclinical studies [Kularatne A., et al. *Design, synthesis, and preclinical evaluation of prostate-specific membrane antigen targeted 99mTc-radioimaging agents. Mol Pharmaceutics,* 2009, 6: 790-800; Lu, G. et al. *Synthesis and SAR of 99mTc/Re-labeled small molecule prostate specific membrane antigen inhibitors with novel polar chelates. Bioorganic & Medicinal Chemistry Letters,* 2013, 23: 1557-1563; Hillier S. M. et al. *99mTc-labeled small-molecule inhibitors of prostate-specific membrane antigen for molecular imaging of prostate cancer. J Nucl Med,* 2013, 54: 1369-1376]. Only the inclusion of a diagnostic image with $^{99m}$Tc has been published, as part of a radiotherapeutic study with $^{177}$Lu in patients [Kratochwil, C. et al. *PSMA-targeted radionuclide therapy of metastatic castration-resistant prostate cancer with Lu-177 labeled PSMA-617. J Nucl Med,* 2016: doi:10.2967/jnumed.115.171397].

To be able to equal the high sensitivity of the PET radionuclides, it is necessary to develop molecules that are more competitive from the viewpoint of affinity and feasibility for being labeled with $^{99m}$Tc, in order to detect tumoral lesions that overexpress PSMA by SPECT techniques and with high sensitivity.

DETAILED DESCRIPTION OF THE INVENTION

Figure 1:
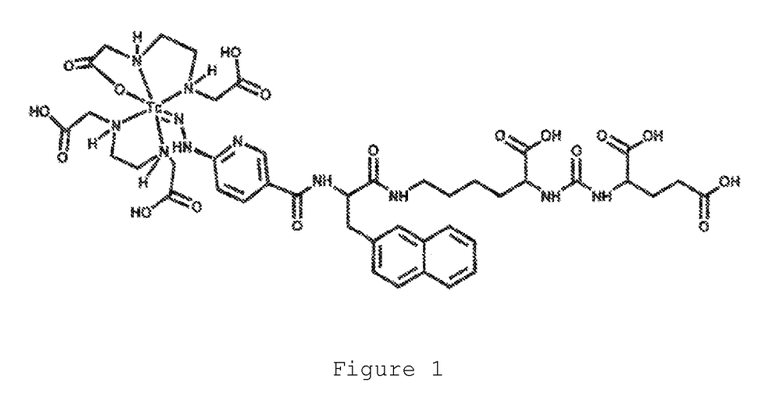
FIG. 1. Structure of 99mTc-ethylenediaminediacetic acid/hydrazinonicotinamide-inhibitor of prostate-specific membrane antigen (99mTc-EDDA/HYNIC-iPSMA).

For purposes of patenting, a new radiopharmaceutical that is an inhibitor of the prostate-specific membrane antigen (iPSMA) is presented, which contains hydrazinonicotinamide (HYNIC) as a chemical group critical in increasing the lipophilicity of the molecule for coupling to the hydrophobic sites of PSMA, combined with the conventional use of HYNIC as a chelating agent for the radiometal $^{99m}$Tc, where ethylenediaminediacetic acid (EDDA) is used for completing the coordination sphere of the radiometal. The new $^{99m}$Tc-EDDA/HYNIC/iPSMA radiopharmaceutical detects, with high affinity in vivo, the PSMA protein overexpressed in prostate cancer cells by SPECT molecular imaging techniques in nuclear medicine. FIG. 1 shows schematically the structure of the radiopharmaceutical to be patented ($^{99m}$Tc-EDDA/HYNIC-iPSMA).

Based on a chemical study of various derivatives that are inhibitors of PSMA, which demonstrated a clear dependence of the properties of binding or affinity on the lipophilicity of the radiopharmaceutical [Kularatne A. et al. *Design, synthesis, and preclinical evaluation of prostate-specific membrane antigen targeted 99mTc-radioimaging agents. Mol Pharmaceutics,* 2009, 6: 790-800], the derivative HYNIC-iPSMA was designed and synthesized, in which the lipophilic properties of the molecule are increased through the presence of the aromatic heterocycle of hydrazinonicotinamide, which in its turn is useful for chelating $^{99m}$Tc. Table 1 below gives, for various inhibitors of PSMA, the comparative results with the radiopharmaceutical to be patented from theoretical calculation of the values of the coefficient of distribution using algorithms of the model of quantitative structure-properties relation (QSPR) for prediction based on the fragment (C Log P), where higher values indicate that the compound is more lipophilic.

Moreover, in the structure of the radiopharmaceutical to be patented, HYNIC also functions as a spacer between the biological recognition site and the radiometal, whereas in other radiopharmaceuticals HYNIC is used exclusively as a bifunctional agent for labeling with $^{99m}$Tc [Decristoforo C. et al. *$^{99m}$Tc-EDDA/HYNIC-TOC: a new $^{99m}$Tc-labelled radiopharmaceutical for imaging somatostatin receptor-positive tumours; first clinical results and intra-patient comparison with 111In-labelled octreotide derivatives,* 2000, *J Nucl Med* 27; 1318-25; Ferro-Flores G. et al. *Preparation and Evaluation of $^{99m}$Tc EDDA/HYNIC-[Lys$^3$]-Bombesin for imaging of GRP Receptor-Positive Tumours. Nucl Med Comm,* 2006, 27:371-376; González-Vázquez A. et al. *Dosimetry and Biokinetics of $^{99m}$Tc-EDDA/HYNIC-Tyr$^3$-Octreotide Prepared from Lyophilized Kits. Appl Rad Isot,* 2006, 64: 792-79; Ortiz-Arzate Z. et al. *Kit preparation and biokinetics in women of $^{99m}$Tc-EDDA/HYNIC-E-[c(RGDfK)]$_2$ for breast cancer imaging, Nucl Med Commun,* 2014, 35:423-32; Medina-García V. et al. *A Freeze-Dried Kit Formulation for the Preparation of Lys$^{27}$ ($^{99m}$Tc-EDDA/HYNIC)-Exendin (9-39)/$^{99m}$Tc-EDDA/HYNIC-Tyr$^3$-Octreotide to Detect Benign and Malignant Insulinomas. Nucl Med Biol,* 2015, 42: 911-916].

Method of Preparation of the Radiopharmaceutical of the Invention

For synthesis of the molecule, initially di-tert.-butyl ester of glutamic acid was used, which was reacted with carbonyl diimidazole (CDI) in the presence of triethylamine (TEA) to form the acylimidazole derivative, which was activated with methyl triflate (MeOTf) for reacting with (S)-tert.-butyl-2-amino-6-(benzyloxycarbonylamine) hexanoate (Cbz-Lys-Ot-Bu) with subsequent deprotection of Cbz via hydrogenolysis, thus obtaining the Glu-Urea-Lys derivative, which was reacted in the solid phase (MBHA resin) with the amino acid Fmoc-β-naphthyl alanine (HBTU/HOBt), followed by 6-Boc-hydrazinopyridine-3-carboxylic acid (Boc-HYNIC)

TABLE 1

INHIBITORS OF PROSTATE-SPECIFIC MEMBRANE ANTIGEN
WITH TUMORAL CAPTURE DEMONSTRATED IN CLINICAL STUDIES

| Chemical structure of potential inhibitors of PSMA | CLogP | Radionuclide used |
|---|---|---|
| | −3.492 | Biological recognition site (PSMA): Glu-NH—CO—NH-Lys (There is no site available for introducing a radionuclide) |
| | −3.652 | $^{99m}$Tc (Diagnostic SPECT) $^{199}$Re (Radiotherapy) Trade name: MIP-1427 |
| | −3.457 | $^{68}$Ga (Diagnostic PET) Trade name: PSMA-11 (HBED-CC) |

TABLE 1-continued

INHIBITORS OF PROSTATE-SPECIFIC MEMBRANE ANTIGEN
WITH TUMORAL CAPTURE DEMONSTRATED IN CLINICAL STUDIES

| Chemical structure of potential inhibitors of PSMA | CLogP | Radionuclide used |
|---|---|---|
| | −4.554 | $^{68}$Ga (Diagnostic PET) $^{177}$Lu (Radiotherapy) Trade name: DOTAGA-(Iy)fk(Sub-KuE) or PSMA I&T |
| | −5.084 | $^{68}$Ga (Diagnostic PET) Trade name: PSMA-10 |

TABLE 1-continued

INHIBITORS OF PROSTATE-SPECIFIC MEMBRANE ANTIGEN
WITH TUMORAL CAPTURE DEMONSTRATED IN CLINICAL STUDIES

Figure 2:
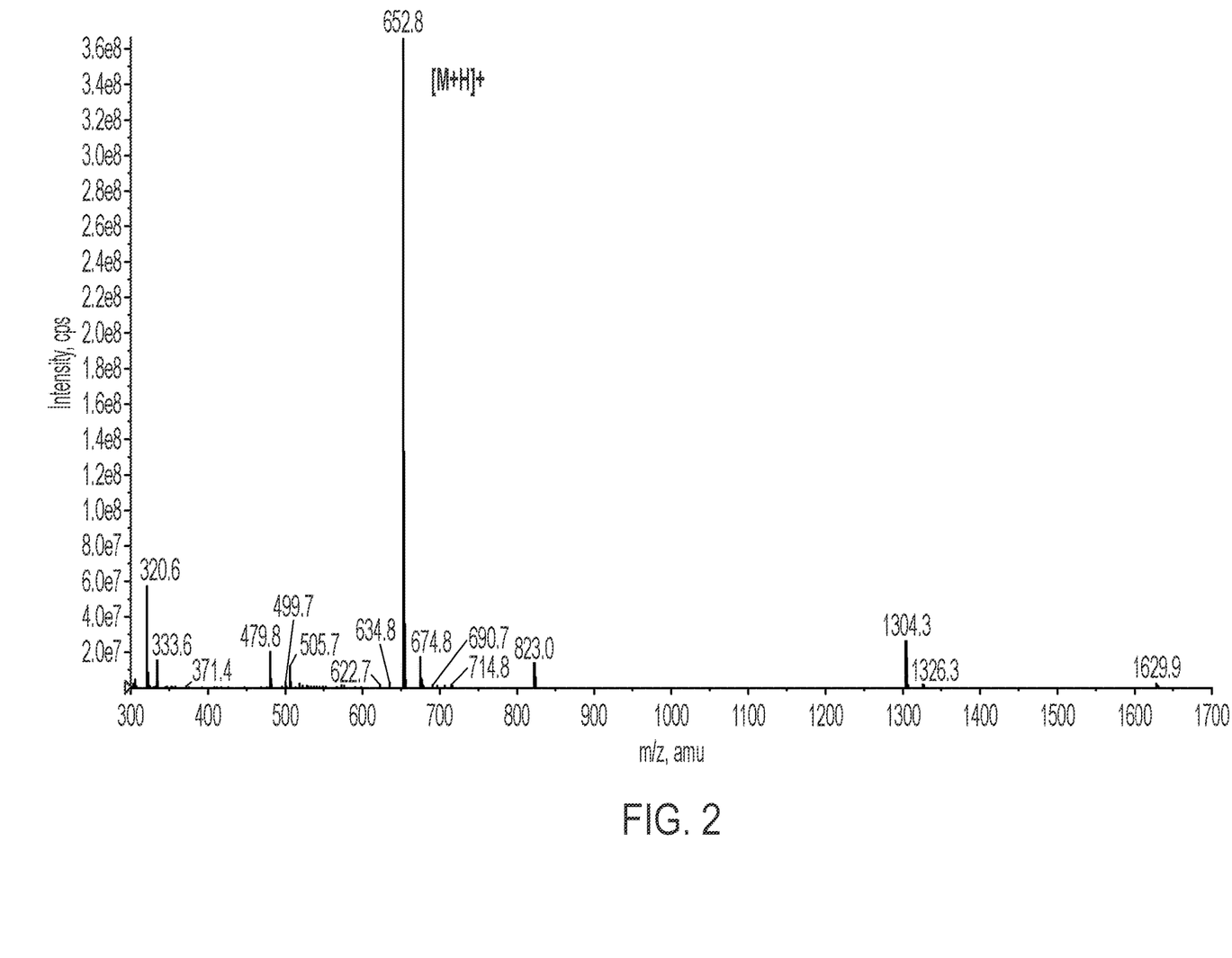
FIG. 2. Mass sectrum of Glu-NH—CO—NH-Lys(β-naphthyl alanine)-HYNIC (HYNIC-iPSMA).

| Chemical structure of potential inhibitors of PSMA | CLogP | Radionuclide used |
|---|---|---|
| [structure] | −5.926 | $^{68}$Ga (Diagnostic PET) $^{177}$Lu (Radiotherapy) Trade name: PSMA-617 or PSMA-DKFZ-617 |
| [structure] | 1.745 | $^{99m}$Tc (Diagnostic SPECT) Name assigned: HYNIC-iPSMA Structure that is the subject-matter of this patent application | in the presence of diisopropylethylenamine (DiPEA) and dimethylformamide (DMF). Finally, the compound was deprotected with TFA, purified by HPLC and lyophilized. The end product was Glu-NH—CO—NH-Lys(β-naphthyl alanine)-HYNIC (HYNIC-iPSMA), which had the expected mass spectrum (FIG. 2).

Reverse-phase HPLC analysis of the lyophilized white solid showed chemical purity of the compound of 98.25%.

Figure 3:
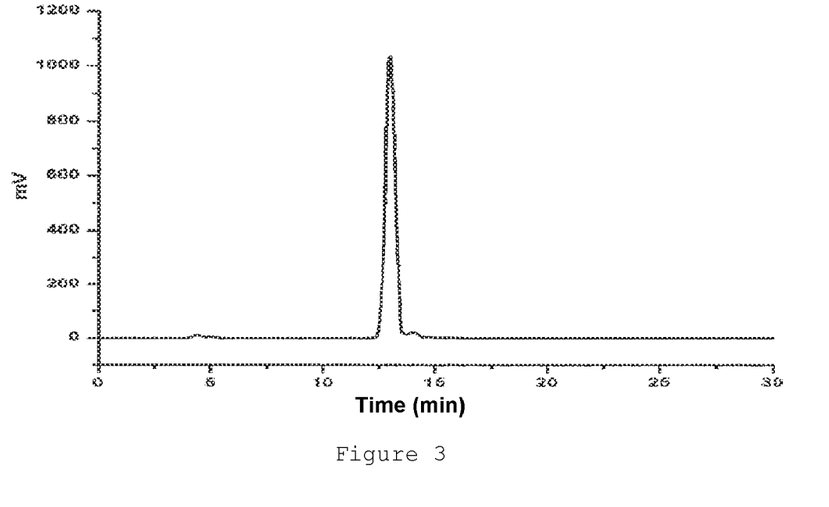
FIG. 3. Reverse-phase HPLC showing purity of compound 99mTc-EDDA/HYNIC-iPSMA.

HYNIC-iPSMA (37.5 µg) was formulated as a lyophilized dosage form containing 10 mg of EDDA, 20 mg of tricine, 20 µg of stannous chloride and 50 mg of mannitol. This formulation, on being reconstituted with 1 mL of 0.2 M phosphate buffer solution, pH 7 and 1 mL of solution of sodium pertechnetate ($^{99m}TcO_4Na$), obtained in situ from a generator of $^{99}Mo/^{99m}Tc$, produces the compound to be patented $^{99m}Tc$-EDDA/HYNIC-iPSMA (FIG. 1) with radiochemical purity greater than 98% determined by reverse-phase HPLC, which has the corresponding radiochromatogram (FIG. 3).

The radiopharmaceutical remains stable with radiochemical purity greater than 95%, 24 h after labeling. In-vitro tests of stability in human serum show binding to serum proteins of 8.3±2.1% and high radiochemical stability (>90%). The affinity of HYNIC-iPSMA, determined by studies of competence in cancer cells positive to the PSMA protein (LN-CaP), showed an $IC_{50}$ of 2.9±0.7 nM.

Figure 4:
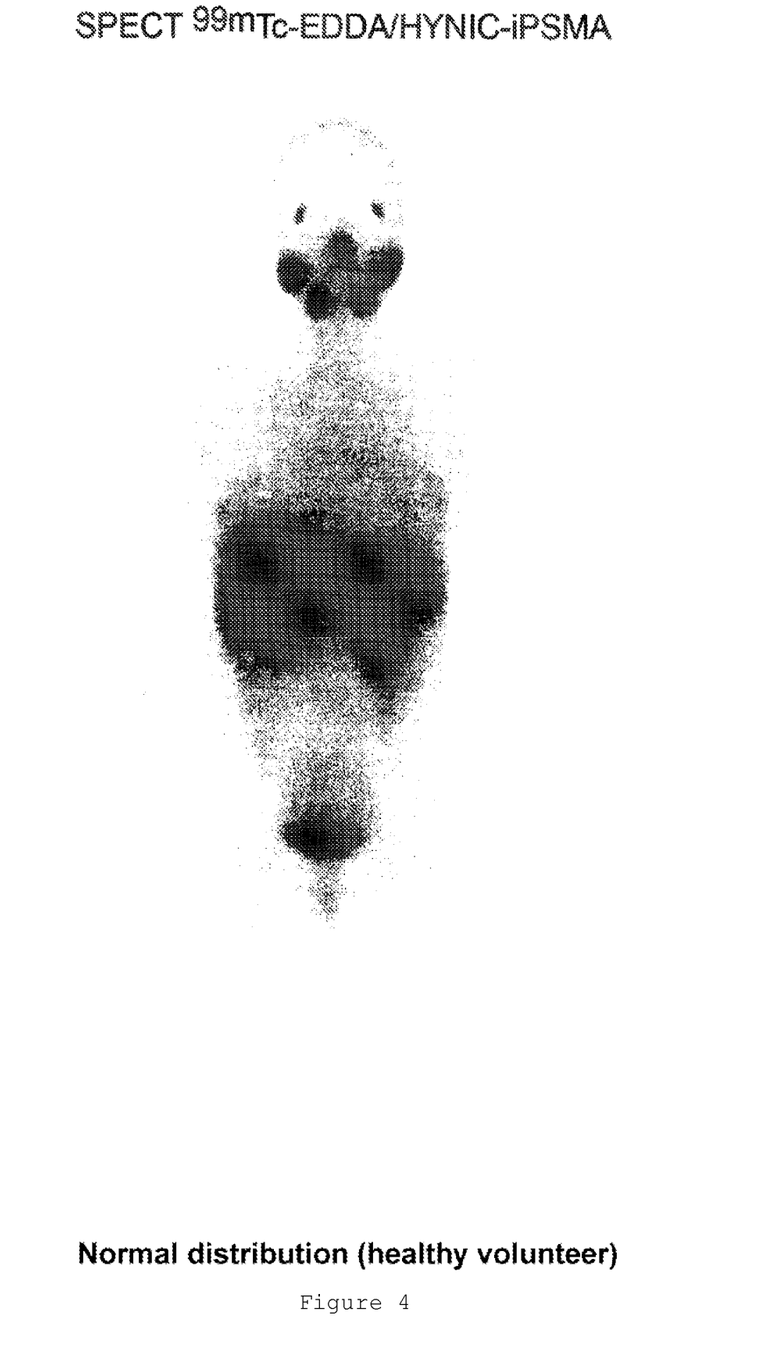
FIG. 4 shows a SPECT image of the radiopharmaceutical 99mTc-EDDA/HYNIC-iPSMA obtained in a healthy volunteer.
Figure 5:
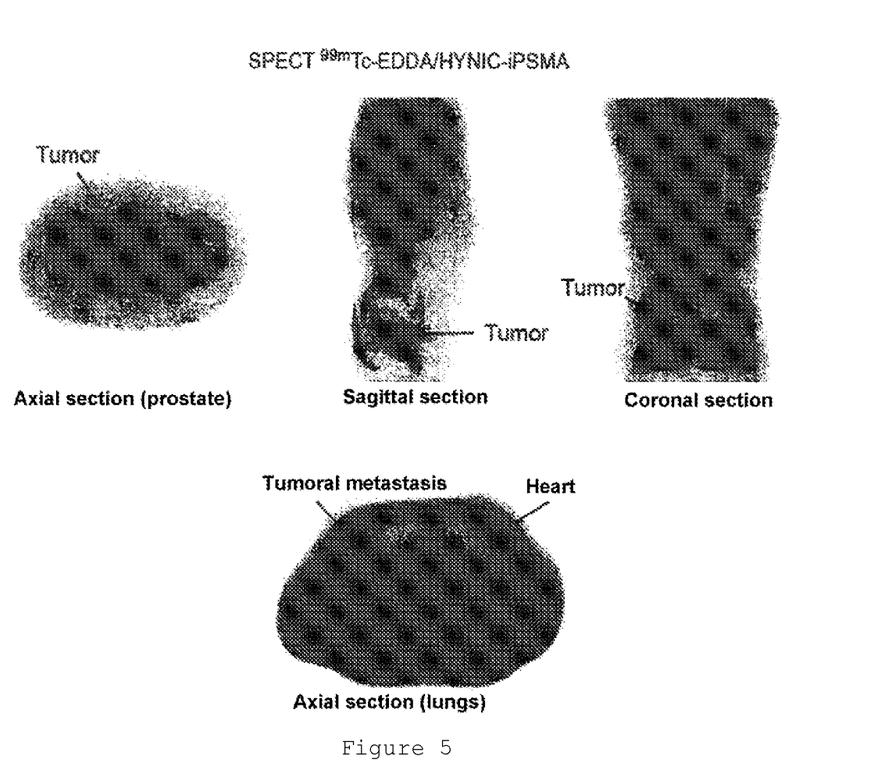
FIG. 5 shows SPECT images of the radiopharmaceutical 99mTc-EDDA/HYNIC-iPSMA obtained in a patient with prostate cancer, confirming the ability of the radiopharmaceutical to detect in vivo PSMA overexpressed in prostate cancer cells.
Figure 6:
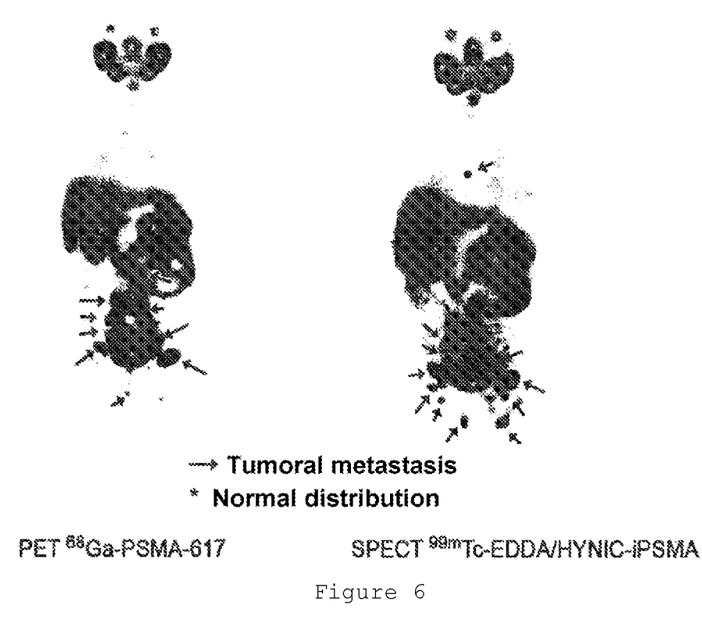
FIG. 6 shows the PET (left) and SPECT (right) image of the same patient with advanced metastatic prostate cancer who was administered both 68Ga-PSMA-617 (PET) and 99mTc-EDDA/HYNIC-iPSMA (SPECT), showing that both radiopharmaceuticals detect tumors and metastases of prostate cancer with high sensitivity, associated with recognition of overexpression of PSMA.

The compound did not display toxicity or adverse effects when it was administered at a dose of 40 mg/kg in balb-C laboratory mice. The tests of biodistribution of $^{99m}Tc$-EDDA/HYNIC-iPSMA in athymic mice with induced LNCaP tumors showed capture in the tumors of 8.7±1.3% of the activity administered per gram of tissue (% ID/g) mainly with elimination by the renal route. Tests of biokinetics and dosimetry in healthy volunteers show rapid clearance from the blood with greater capture and renal excretion, lower hepatic capture and high capture in the parathyroid, salivary and lacrimal glands, with a mean effective dose of 4±2 mSv per 740 MBq administered. FIG. 4 shows a SPECT image of the radiopharmaceutical $^{99m}Tc$-EDDA/HYNIC-iPSMA obtained in a healthy volunteer. FIG. 5 shows a SPECT image of the radiopharmaceutical $^{99m}Tc$-EDDA/HYNIC-iPSMA obtained in a patient with prostate cancer, confirming the ability of the radiopharmaceutical to detect in vivo PSMA overexpressed in prostate cancer cells. Finally, FIG. 6 shows the PET and SPECT image of the same patient with advanced metastatic prostate cancer who was administered both $^{68}Ga$-PSMA-617 (PET) and $^{99m}Tc$-EDDA/HYNIC-iPSMA (SPECT), showing that both radiopharmaceuticals detect tumors and metastases of prostate cancer with high sensitivity, associated with recognition of overexpression of PSMA. This image confirms, and is the main evidence, that because of its increased properties of affinity owing to the lipophilicity of the incorporated HYNIC molecule, $^{99m}Tc$-EDDA/HYNIC-iPSMA is able to equal the high imaging sensitivity of the PET radionuclides in the detection of tumoral lesions that overexpress PSMA.

In conclusion, $^{99m}Tc$-EDDA/HYNIC-iPSMA is obtained with the following characteristics:

Radiochemical purity greater than 95%

Ability of the radiopharmaceutical to detect in vivo and specifically, tumors that overexpress the prostate-specific membrane antigen by single-photon emission tomography (SPECT) in nuclear medicine.

In addition to molecular recognition of the Glu-NH—CO—NH— sequence of the radiopharmaceutical to be patented based on $^{99m}Tc$, it has the ability to bind significantly to and detect with high sensitivity, tumors and metastases of prostate cancer, owing to the increased lipophilicity conferred by the presence of the hydrazinonicotinamide (HYNIC) molecule, which allows it to interact effectively in coupling to the hydrophobic active site of the enzyme PSMA for detecting it by SPECT imaging.

The invention claimed is:

1. A compound comprising the following structural formula:

(HYNIC-iPSMA)

2. A radiopharmaceutical comprising the compound of claim 1 and a radionuclide selected from the group consisting of $^{99m}Tc$ and $^{188}Re$.

3. The radiopharmaceutical of claim 2, for use as a radiodiagnostic agent.

4. A kit comprising the compound of claim 1 (HYNIC-iPSMA) formulated as a lyophilized dosage form containing 10 mg of EDDA, 20 mg of tricine, 20 µg of stannous chloride and 50 mg of 15 mannitol, for use in radiolabelling.

5. A method of in vivo imaging a tumor expressing prostate-specific membrane antigen (PSMA) protein in a patient, the method comprising administering to the patient an effective amount of the radiopharmaceutical of claim 2, wherein said radionuclide is $^{99m}Tc$, and detecting said radiopharmaceutical agent by SPECT molecular imaging techniques.

6. The method of claim 5, wherein said in vivo imaging is effective to detect prostate cancer metastatic lesion sites.

7. A radiotherapeutic method comprising administering a therapeutically effective amount of the radiopharmaceutical according to claim 2, wherein said radionuclide is $^{188}Re$, to a subject in need of treatment of prostate cancer.

* * * * *